US00PP34354P2

(12) United States Plant Patent
Horvath

(10) Patent No.: US PP34,354 P2
(45) Date of Patent: Jun. 14, 2022

(54) ***MONARDA BRADBURIANA* PLANT NAMED 'MIDNIGHT OIL'**

(50) Latin Name: *Monarda bradburiana*
Varietal Denomination: Midnight Oil

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 17/300,586

(22) Filed: Aug. 30, 2021

(51) Int. Cl.
*A01H 5/02* (2018.01)
*A01H 6/14* (2018.01)

(52) U.S. Cl.
USPC ..... Plt./455

(58) Field of Classification Search
USPC ..... Plt./263.1, 455
See application file for complete search history.

(56) References Cited

PUBLICATIONS

Intrinsic Perennial Gardens, Inc. 2021 Wholesale Catalog. file:///C:/Users/kredden/Desktop/Intrinsic%20Wholesale%202021%20catalog.pdf. 39 pgs. (Year: 2021).*
Intrinsic Introductions 2021 Introductions Catalog. file:///C:/Users/kredden/Desktop/Intrinsic%20Introductions%202021%20catalog.pdf. 31 pgs. (Year: 2021).*

* cited by examiner

*Primary Examiner* — Karen M Redden

(57) ABSTRACT

A new, distinct *Monarda bradburiana* plant, named 'Midnight Oil', as shown and described, characterized by the combination of chocolate purple N187 A colored new growth, glossy green foliage, and plants that are resistant to foliar diseases.

1 Drawing Sheet

Figure 1:
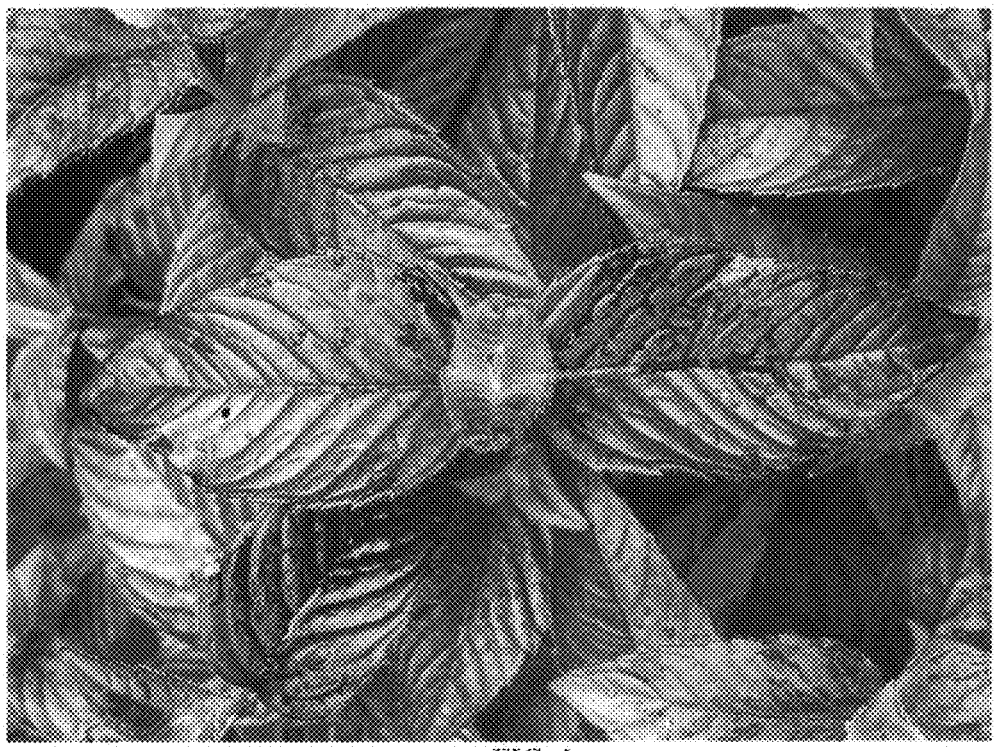

Latin name: *Monarda bradburiana.*
Cultivar name: 'Midnight Oil'.

BACKGROUND OF THE INVENTION

The present invention relates to a new and distinct cultivar of *Monarda bradburiana* plant, botanically known as *Monarda bradburiana* .and hereinafter referred to by the name 'Midnight Oil'. The new *Monarda bradburiana* plant is a product of a planned breeding program conducted by the inventor in Hebron, Ill., USA. The objective of the breeding program is to create vigorous new *Monarda* plants that are resistant to powdery mildew and other common diseases in *Monarda* and was selected for the chocolate purple foliage of its new growth and glossy green foliage. The new *Monarda bradburiana* plant was discovered and selected by the inventor as a single flowering plant from within the progeny of the stated cross-pollination of an unnamed plant of *Monarda bradburiana* as the female parent and an unnamed plant of *Monarda bradburiana* as the male parent, grown in a controlled environment in Hebron, Ill., USA during the summer of 2017. Asexual reproduction of the new *Monarda bradburiana* plant by softwood cuttings in Hebron, Ill., USA since the summer of 2018, have shown that the unique features of this new *Monarda bradburiana* plant are stable and reproduced true to type in successive generations. No plants of the new *Monarda bradburiana* have been sold in this country, or anywhere in The world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

Plants of the new *Monarda bradburiana* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Midnight Oil'.

These characteristics in combination distinguish 'Midnight Oil' as a new and distinct. *Monarda bradburiana* plant:

1. New growth, colored: N187 A.
2. Glossy deep-green mature foliage that remains free of all foliar diseases.
3. Resistant to powdery mildew.

Plants of the new *Monarda bradburiana* differ primarily from plants of 'Blue Moon' U.S. Plant Pat. No. 29,549 in the following characteristics:

1. Plants of the new *Monarda bradburiana* have pink flowers while 'Blue Moon' has lavender blue flowers.
2. Leaves of plants of the new *Monarda bradburiana* are darker in color than leaves of plant 'Blue Moon'.
3. Plants of the new *Monarda bradburiana* differ primarily from plants of 'Mojo' U.S. Plant Pat. No. 29,982 in the following characteristics:
   a. Plants of the new *Monarda bradburiana* have pink flowers while 'Mojo' has purple flowers.
   b. Leaves of the new *Monarda bradburiana* are glabrous and color N187 A, while 'Mojo' are pubescent and color 200A.

Plants of the new *Monarda bradburiana* can be compared to plants of the female parent an unnamed plant of *Monarda bradburiana.*

In side-by-side comparisons plants of the new *Monarda bradburiana* differ from plants of the female parent an unnamed plant of *Monarda bradburiana* in the following characteristics:

1. Plants of the new *Monarda bradburiana* are more vigorous than plants of the unnamed female parent plant of *Monarda bradburiana.*
2. Foliage of plants of the new *Monarda bradburiana* have chocolate-purple new foliage and glabrous deep-green foliage that differs from plants of the unnamed female parent plant of *Monarda bradburiana* having mostly green and slightly pubescent foliage.

Plants of the new *Monarda bradburiana* can be compared to plants of the male parent an unnamed plant of *Monarda bradburiana.*

In side-by-side comparisons plants of the new *Monarda bradburiana* differ from plants of the male parent an unnamed plant of *Monarda bradburiana* in the following characteristics:

1. Plants of the new *Monarda bradburiana* are more vigorous than plants of the unnamed male parent plant of *Monarda bradburiana.*
2. Foliage of plants of the new *Monarda bradburiana* have chocolate-purple new foliage and glabrous deep-green foliage that differs from plants of the unnamed male parent plant of *Monarda bradburiana* having mostly green and glabrous foliage.

DESCRIPTION OF PHOTOGRAPHS

The accompanying colored photographs illustrate the overall appearance of the new *Monarda bradburiana* plant showing the colors as true as it is reasonably possible to obtain in colored reproductions of this type. Colors in the photographs may differ slightly from the color values cited in the detailed botanical description which accurately describe the actual colors of the new *Monarda bradburiana* plant.

FIG. 1. Close up of the new foliage on a one-year old plant in Hebron, Ill. USA. FIG. 1 also shows the mature green glabrous foliage.

Figure 2:
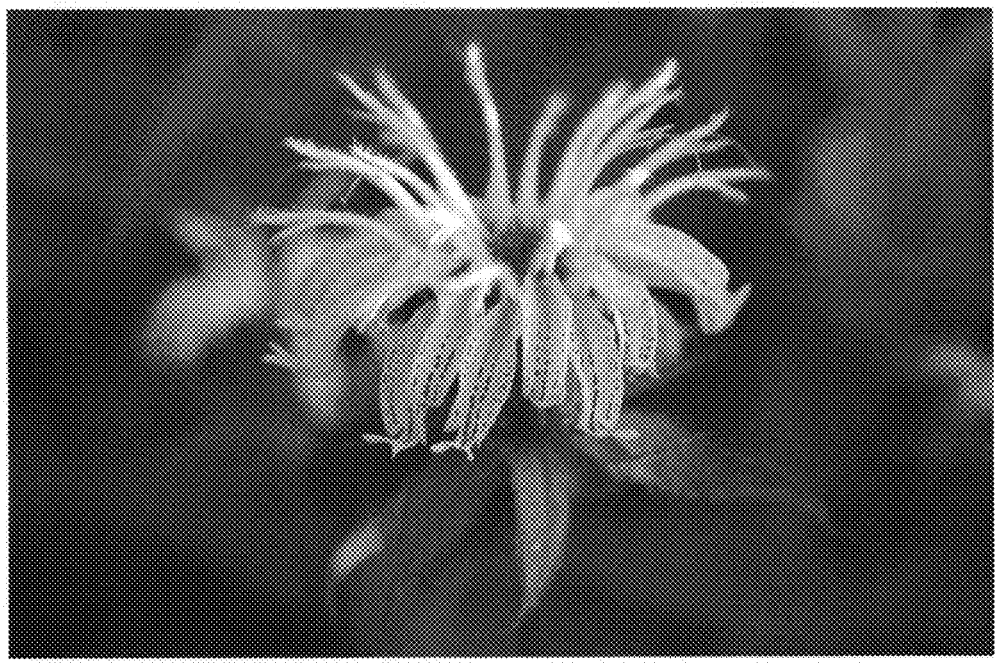

FIG. 2. Close up flower in June on a one-year old plant in Hebron, Ill. USA.

DETAILED BOTANICAL DESCRIPTION

The aforementioned photographs and following observations, measurements and values describe one-year old plants grown during the summer in an outdoor nursery in Hebron, Ill. USA and under typical production conditions. In the detailed description, color references are made to The Royal Horticultural Society Colour Chart, 2001 Edition, except where general terms of ordinary dictionary significance are used.

Plant description:

Botanical classification: *Monarda bradburiana.*

Parentage:

*Female, or seed, parent.*—*Monarda bradburiana*, unnamed seedling.

*Male, or pollen, parent.*—*Monarda bradburiana*, unnamed seedling.

Propagation:

*Type cutting.*—By softwood cuttings.

*Time to initiate roots, summer.*—About two weeks.

*Time to produce a rooted young plant, summer.*—About two months.

*Root description.*—Fine, fibrous; grey brown in color.

*Rooting habit.*—Freely branching; dense.

Plant description:

*Plant and growth habit.*—Perennial, upright and outwardly spreading plant form; broad; basal branching habit; moderately vigorous growth habit.

*Plant height.*—45 cm.

*Plant width.*—60 cm.

*Lateral branch description.*—Length: About 11 cm. Diameter: About 2 mm. Internode length: About 5 cm. Strength: Strong. Aspect: Upright. Texture: Glabrous. Color: 148 A to as dark as N79 A.

Foliage description:

*Arrangement.*—Opposite, simple.

*Length.*—About 90 mm.

*Width.*—About 45 cm.

*Shape.*—Ovate.

*Apex.*—Acute.

*Base.*—Rounded to truncate.

*Margin.*—Serrate.

*Texture, upper and lower surfaces.*—Glabrous.

*Venation pattern.*—Pinnate.

*Venation color.*—117 D.

*Color.*—Developing leaves, upper surface: N187 A. Developing leaves, lower surface: 137 A. Mature leaves, upper surface 137 A, Mature leaf, lower surface 146 C.

*Petiole size: length.*—About 5 mm and diameter — About 2 mm.

*Petiole color, upper and lower surface.*—Varies from 147 D to red N187 A.

Flower description:

*Flower form, arrangement and flowering habit.*—Single labiate and sessile flowers arranged in terminal globular spikes; flowers face outwardly; freely flowering habit with about 150 flowers developing per inflorescence.

*Natural flowering season.*—Continuous flowering from early June to July in Hebron, Ill., USA.

*Flower longevity on the plant.*—About five days; flowers not persistent.

*Fragrance.*—Faintly fragrant; spicy, pleasant.

*Flower buds.*—Length: About 15 mm. Diameter: About 1 mm. Shape: Narrowly oblanceolate; Curved. Color: N155 C.

*Inflorescence size.*—Length: About 20 mm. Diameter: About 25 mm.

*Inflorescence Bracts, typical and observed.*—Arrangement: subtending, Number: 5, Shape: ovate, Length: about 20 mm. Width: 5 mm. Apex: acute, Margin: entire, Bract color: N77 C Base: truncate, Color: At the base N144 C.

*Flowers.*—Diameter: About 1-2 mm. Depth: About 4 cm.

*Petals.*—Arrangement: Labiate; upper lip hooded; lower lip, a single lobe; lips fused. Length, upper and lower lips: About 4 cm. Width, upper lip: About 1 mm. Width, lower lip: About 4 mm. Shape, upper lip: Lanceolate; apex, narrowly acute. Shape, lower lip: Oblanceolate; apex, aristate. Margin, upper and lower lips: Entire. Texture, upper and lower surfaces: Glabrous. Color: When opening, upper and lower surfaces of upper lip: 75 A becoming 75 B, lower lip: N155 B and when. fully opened, upper and lower surfaces: N155 B to near white, lower lip: N155 B.

*Sepals*.—Arrangement: Five in. a single whorl: fused, tubular. Length: About 9 mm. Width: About 2 mm. Apex: Narrowly acute. Margin: Entire. Texture, upper and lower surfaces: glabrous. Color: When opening, upper and lower surfaces and fully opened, upper and lower surfaces: N155 B with purple spots of N79 C & 71 A. down the middle toward the base color.

*Reproductive organs*.—Stamens: Quantity per flower. Two. Filament length. About 2 cm. Filament color: Close to N155 B. Anther length: About 1 mm. Anther shape: Narrowly elliptic. Anther color: Close to 71 A. Pollen amount: Scarce. Pollen color: 96 D. Pistils: Quantity per flower. One. Pistil length: About 25 mm. Stigma shape: Cleft. Stigma color: N155 B. Style length: 2.5 cm Style color N155 B. Ovary color green.

*Seed and fruit*.—Seed and fruit production have not been observed.

Disease resistance: Plants of the new *Monarda bradburiana* have been observed to be resistant to powdery mildew common to other *Monarda* plants and species.

Pest resistance: Plants of the new *Monarda bradburiana* have not been observed to be resistant to pests and other pathogens common to *Monarda bradburiana* plants.

Garden performance: Plants of the new *Monarda bradburiana* have exhibited good tolerance to rain and wind, have been observed to be hardy to USDA Zone 5 and to tolerate high temperatures of about 35° C.

I claim:

1. A new, distinct *Monarda bradburiana* plant, named 'Midnight Oil', as shown and described, characterized by the combination of chocolate purple N187 A colored new growth, glossy green foliage, and plants that are resistant to foliar diseases compared to the seed parent.

* * * * *